United States Patent [19]

Palsson et al.

[11] Patent Number: 5,616,487
[45] Date of Patent: Apr. 1, 1997

[54] STABILIZED RETROVIRUS COMPOSITIONS

[75] Inventors: Bernhard O. Palsson; Timothy M. Eisfeld, both of Ann Arbor, Mich.

[73] Assignee: Aastrom Biosciences, Inc., Ann Arbor, Mich.

[21] Appl. No.: 307,862

[22] Filed: Sep. 15, 1994

[51] Int. Cl.$^6$ .............................. C12N 7/01; C12N 5/10
[52] U.S. Cl. ..................... 435/235.1; 435/172.3
[58] Field of Search .................. 435/69.1, 235.1, 435/172.1, 173.3, 240.2, 240.3, 320.1

[56] References Cited

U.S. PATENT DOCUMENTS

| | | | |
|---|---|---|---|
| 4,094,969 | 6/1978 | Batzer et al. | 424/78.01 |
| 4,314,997 | 2/1982 | Shanbrom | 514/2 |

OTHER PUBLICATIONS

Dea et al., "Physicochemical and Biological Properties of Neonatal Calf Diarrhea Coronaviruses Isolated in Quebec and Comparison with the Nebraska Calf Coronavirus", Am. J. Vet. Res., vol. 41, No. 1 pp. 23–29, 1980.
Strauss and DeRose, "Stabilization of lipid bilayer vesicles during freeze/thawing by single–chain detergents." *Biophysical Journal* 57:474a (1990).
McPherson et al., "Pluronic F–68 protects free fatty acid (FFA) damages red blood cells (RBC'S) against mechanical fragility." *Federation Proceedings* 46(3):535 (1987).
Massaro and Cherry, "Effects of pluronic F–68 on planar lipid bilayer permeability following fusion with sarcoplasdmic reticulum vesicles." *FASEB Journal* 7(3):A359 (1993).
Farnsworth et al., "The glass effect on red blood cells can be prevented by pluronic F–68." *FASEB Journal* 7(4):A682 (1993).
Mizuno et al., "Stabilization of biliary lipid particles by ursodeoxycholic acid." *Digestive Diseases and Sciences* 38(4):684–693 (1993).
Strauss et al., "The interaction of saccharides with lipid bilayer vesicles: stabilization during freeze–thawing and freeze–drying." *Biochimica et Biophysica Acta* 858:169–180 (1986).
Zhang et al., "Effect of pluronic F–68 on the mechanical properties of mammalian cells." *Enzyme Microb. Technol.* 14:980–983 (1992).
Carlsson et al., "Physiochemical stabilization of lipid microspheres by coating with polysaccharide derivatives." *Bulletin of the Chemical Society of Japan* 62:791–796 (1989).
Israelachvili, "Intermolecular and Surface Forces", Second Edition, Academic Press Limited 375–383 (1992).
Kotani et al., "Improved methods of retroviral vector transduction and production for gene therapy." *Human Gene Therapy* 5:19–28 (1994).
Richard Mulligan "The basic science of gene therapy." *Science* 260:926–932 (1993).
Springett et al., "Infection efficiency of T lymphocytes with amphotropic retroviral vectors is cell cycle dependent." *J. Virol.* 63:3865–9 (1989).
Wang and Hanson, "Parenteral formulations of proteins and peptides: stability and stabilizers." *J. of Parenteral Science & Technology* 42:s4–s6 (1988).
Danos and Mulligan, "Safe and efficient generation of recombinant retroviruses with amphotropic and ecotropic host ranges." *Proc. Natl. Acad. Sci USA* 85:6460–6464 (1988).

*Primary Examiner*—David Guzo
*Attorney, Agent, or Firm*—Campbell & Flores LLP

[57] ABSTRACT

The present invention provides a stabilized virus, which is modified using a stabilizing agent. The invention also provides a process for producing a stabilized virus by culturing viral producing cells with a stabilizing agent at a temperature below 37° C. The invention further provides methods to introduce an exogenous nucleotide sequence into a cell using a stabilized virus containing the exogenous nucleotide sequence. The invention also provides methods for administering an exogenous nucleotide sequence to a subject using a stabilized virus containing the exogenous nucleotide sequence. The invention further provides a method to produce a protein by infecting a cell with a stabilized virus containing a exogenous nucleotide sequence encoding the protein and then isolating the protein produced by the infected cells.

15 Claims, No Drawings

STABILIZED RETROVIRUS COMPOSITIONS

BACKGROUND OF THE INVENTION

1. Field of the Invention

This invention relates generally to genetic engineering, and more specifically, to gene therapy and to increasing viral stability.

2. Background Information

The goal of gene therapy is to treat disease by transferring genetic information into a diseased target cell. In comparison to conventional pharmaceutical therapy, gene therapy has greater potential for reduced treatment toxicity and for curing the disease. Gene therapy has been a major focus of biomedical research since the early 1980s when various methods were developed to introduce manufactured genes into cells. Gene therapies are under development for cancer, cardiovascular diseases, blood diseases, infectious diseases, neurologic disorders, inflammatory diseases and various genetic diseases. Approximately three million people each year in developed countries may benefit from gene therapy.

Methods to introduce exogenous genetic information into cells include physico-chemical as well as viral-mediated approaches. In general, viral-mediated approaches have received a great deal of attention because they can efficiently infect cells that express the appropriate viral receptors on the cell surface and because a wide variety of recombinant virus are available that differ in their host range and cell type infectivity. A wide variety of recombinant viruses have been successfully used to deliver exogenous genetic information to cells in vivo and in vitro. In particular, replication incompetent retroviruses have proved useful for gene therapy because they can infect most cell types and allow the stable introduction of genetic material into a chromosome of the infected target cell.

Retroviral infection of a cell, leading to stable integration of a viral nucleic acid molecule in the chromosome of the cell, is a process unique among RNA viruses. The process of retroviral infection begins with contact between the cell and the virus via specific receptor/ligand interactions. Following contact, the viral RNA is internalized and transcribed into DNA by the enzyme reverse transcriptase. The viral DNA then enters the nucleus and finally is integrated into the target cell's chromosomes. This last step requires cell division, which, for mammalian cells, occurs most efficiently at 37° C.

The requirement for a target cell to undergo cell division for integration of the retroviral DNA limits the potential for high efficiency infection because only a small fraction of the cells in an unsynchronized population undergo cell division at any given time. Thus, high efficiency infection rates can be achieved only if active virus is present in a cell culture long enough for all of the cells to undergo cell division. Unfortunately, most recombinant retroviruses have a half-life at 37° C. that is substantially less than the duration of one cell cycle. As a result, insufficient active virus is available for infection at the later rounds of cell division. This insufficiency could be prevented if high concentrations of retrovirus can be added to the cells in culture, or if retrovirus possessing a significantly-extended half-life can be used. A longer viral half-life reduces the need to concentrate the virus at later steps in processing.

Thus, there exists a need for methods to increase the stability of recombinant viruses so that a large number of target cells can be efficiently infected for gene therapy. The present invention satisfies this need and provides related advantages as well.

SUMMARY OF THE INVENTION

The present invention provides a stabilized virus, which is modified using a stabilizing agent. The invention also provides a process for producing a stabilized virus by culturing viral producing cells with a stabilizing agent at a temperature below 37° C. In addition, the invention provides methods to produce a stabilized virus by producing the virus at a temperature below 37° C. and then adding the stabilizing agent.

The invention further provides methods to introduce an exogenous nucleotide sequence into a cell using a stabilized virus containing the exogenous nucleotide sequence. The invention also provides methods for administering an exogenous nucleic acid sequence to a subject using a stabilized virus containing the exogenous nucleic acid sequence.

The invention also provides methods to produce a protein by infecting a cell with a stabilized virus containing a nucleic acid sequence encoding the protein. Additionally, the invention provides for isolating the protein produced by the infected cells.

DETAILED DESCRIPTION OF THE INVENTION

This present invention provides both compositions and processes to produce a virus with greatly improved properties for infecting cells. In particular, the stabilized virus of the present invention shows greater infectivity half-life in culture at 37° C. than does a non-stabilized virus.

As used herein, the term "stabilized virus" means a virus that maintains infectivity over a longer period of time than one that is not stabilized. For example, incubation at 37° C. results in a loss in infectivity over time. However, a stabilized virus will retain more of its infectivity after incubation at 37° C. as compared to a virus produced at 37° C. without the stabilizing agent. A loss of viral infectivity can also occur by exposing the virus to particular chemicals or by processing, such as by concentrating or storing the virus. A stabilized virus as disclosed herein can resist loss of viral infectivity to at least one type of treatment.

As used herein, "infectious virus" is a virus capable of transferring all or a portion of it's viral vector into a cell, resulting in expression of an exogenous nucleotide sequence incorporated in the viral vector. The infectivity of a virus would thus be a measure of the ability of the virus to mediate transfer and expression of an exogenous nucleotide sequence in a cell. As used herein, "infectivity half-life" refers to the period of time over which the infectivity of a population of virus particles falls to half its original infectivity.

As used herein, the term "stabilizing agent" means a compound or combination of compounds that when exposed to a virus produced under certain temperatures results in a stabilized virus. For example, a stabilizing agent can be a compound such as a lipid or a surfactant that stabilizes the viral lipid envelope. An example of a stabilizing agent is the product Lipid Concentrate (Gibco/BRL, Gaithersburg, Md., catalogue no: 21900-014). Lipid Concentrate is a formulation that contains cholesterol, cod liver oil, Pluronic® F-68, d-α-tocopherol acetate and Tween 80™. In all experiments combined, the 37° C. infectivity half-lives of retroviruses were increased about 10–100% when the retroviruses were produced at 29° C. in culture medium supplemented with Lipid Concentrate (representative experiments are shown in Table I).

A stabilizing agent can also be a single compound such as the surfactant Pluronic® F-68, which is a component of Lipid Concentrate. Pluronic® F-68 is a non-ionic surfactant which is a member of the α-hydro-ω-hydroxypoly(oxyethylene)poly(oxypropylene)poly(oxyethylene) block copolymer group of compounds. Pluronic® F-68 is also known as Poloxamer 188 or Exocorpol (see Merck Index)]. Addition of Pluronic® F-68, with or without additional supplements to the culture medium of two different retroviral producing cell lines, and incubation of the culture at 29° C. resulted in production of a stabilized retrovirus with a 39% to 53% average increase in 37° C. infectivity half-life compared with virus produced in standard culture medium at 37° C. (see Tables II and III). As used herein, "surfactant" refers to a class of compounds that are surface active agents that can alter the surface tension of a liquid by generally lowering it.

The viral envelope also contains membrane proteins that can be required for infectivity. Thus, a stabilizing agent can also be a compound that stabilizes the proteins present in the viral envelope. Protein and peptide stabilizing compounds are well known in the art and include, lipids, surfactants, such as nonionic surfactants, polyols, such as carbohydrates, reducing agents, antioxidants, metals, chelating agents, amino acids and serum albumin. The stabilizing agent can also include a compound which increases viral infectivity half-life by stabilizing both the lipid and protein in the viral envelope (see, for example, Wang and Hanson *J. Paren. Sci. Tech.* 42:S1–S26 (1988), which is incorporated herein by reference). In addition, the stabilizing agent can also include a compound that stabilizes lipid and a compound that stabilizes protein.

In general, retroviruses are characterized, in part, by their limited ability to infect cells at 37° C. because at this temperature, the infectivity half-life of the virus is significantly less than the time of one mammalian cell cycle. For example, the infectivity half-life for murine retrovirus at 37° C. is about 5 hours (Sanes et al., *EMBO J.*, 5:3133–3142 (1986)), while the time for a typical normal diploid mammalian cell cycle ranges from 24 to 72 hr (see Freshney, *Culture of Animal Cells—A Manual of Basic Technique*, 2nd edition, Alan R. Liss, Inc. New York, (1987)). Thus, over 90% of the viral infectivity titer is lost during the time it takes for one mammalian cell cycle (Kotani et al., *Human Gene Therapy*, 5:19–28 (1994)).

A short infectivity half-life for virus at 37° C. also limits the viral titer attainable in a retrovirus-producing culture incubated at the same temperature. When a production culture reaches the maximum cell density, the rate of new virus particle generation reaches a peak level. At this point, the rate of loss of viral infectivity titer via physical and chemical decomposition of key components of the retrovirus particle matches the rate of new infectious virus particle generation, causing the viral titer to peak (Mulligan, *Science* 260;926–932 (1993)). The rate of loss of viral infectivity titer is proportional to the quantity of viral infectivity titer and is inversely proportional to the viral infectivity half-life. Thus, the maximum titer attainable in a retrovirus-producing culture is limited, in part, by the viral infectivity half-life. The longer the half-life, the greater the maximum titer.

Increased retroviral stability provides several advantages. For example, a longer viral infectivity half-life enables exposure of the target cells to significant viral titer through more cell cycles, thus, increasing the opportunity for successful infection of a greater percentage of the target cells.

In addition, since the maximum virus titer attainable from the harvest of a virus-producing culture is directly proportional to the viral infectivity half-life, a higher initial titer reduces the need to concentrate the virus and simplifies downstream processing of the viral broth.

Many types of viruses including retroviruses are released by budding through the plasma membrane of the infected cell. During budding, the virus acquires an external envelope composed mainly of lipids, the composition of which is similar to the plasma membrane of the infected cell. Plasma cell membranes are typically composed of cylindrically-packed double-chain lipids with small head-group areas and saturated rigid chains which are suited for planar membranes. However, since the radius of the curvature of the lipid envelope of a retrovirus is about 50 nm, this forces the lipid viral envelope to acquire a spherical rather than planar conformation. The reduced radius of curvature may result in significant thermodynamic stress in the viral envelope which can have a negative impact on viral stability.

To achieve maximum flexibility, a lipid envelope should contain double-chain molecules of large head-group areas and fluid chains that have a truncated conical critical packing shape suited for a highly flexible bilayer. Examples of such lipids include phosphatidyl choline, phosphatidyl serine, phosphatidyl glycerol, phosphatidyl inositol, phosphatidic acid, dihexadecyl phosphate and dialkyl dimethyl ammonium salts (Israelachvili, J. N. *Intermolecular and Surface Forces*, second Edition (John Wiley and Sons Limited, 375–383, 1992)).

As used herein, a "virus" is an infectious unit comprising either viral DNA or RNA enclosed in a protective coat. The viral nucleic acid can contain information necessary for viral replication in a susceptible host cell or can be a replication incompetent virus that lacks critical genetic information needed for replication. A recombinant virus that contains a nucleic acid molecule modified by recombinant DNA techniques is also included within the meaning of a virus. A recombinant virus that has viral nucleotide sequences deleted or that contains exogenous nucleotide sequence derived from another type virus or cell is also included within the meaning of the term virus.

A stabilized virus of the present invention can be a DNA or an RNA virus. RNA viruses can include, for example, poliovirus or a retrovirus, while DNA viruses can include, for example, SV-40 virus, polyoma virus, adenovirus, adeno-associated virus, Epstein bar virus, vaccinia virus, papilloma virus and herpes virus. Viral vectors that have been modified to incorporate genes and produce recombinant virus are known in the art and described, for example, by Krieger, *Gene Transfer and Expression: A Laboratory Manual*, (W. H. Freeman and Company, 1990); Goeddel, *Methods in Enzymology*, vol 185, (Academic Press, 1990); and Stoker, In *Molec. Virol., A Practical Approach* (eds. Davison and Elliott, IRL Press, 1993), all three of which are incorporated herein by reference and are included within the scope of this invention. Methods to modify viral vectors to eliminate particular viral functional nucleotide sequences and to insert exogenous nucleotide sequences are also known in the art (see, for example, Sambrook et al., *Molecular Cloning: A laboratory manual* (Cold Spring Harbor Laboratory Press 1989), which is incorporated herein by reference).

Typical recombinant viral expression vectors contain cloning sites for efficient incorporation of an exogenous nucleic acid sequence. As used herein, the term "exogenous nucleotide sequence" means a sequence of nucleotides that is normally not associated with the wild-type viral vector. An exogenous nucleotide sequence can encode a protein or an RNA molecule. An exogenous nucleotide sequence encoding a protein can be a cDNA gene sequence or a genomic sequence and can be eukaryotic, viral or prokaryotic in origin. A large variety of cellular genes are available in the art which can be cloned into a viral vector as an exogenous nucleotide sequence (see, for example, Morgan et al. *Adv. Drug Deliv. Rev.* 12:143–158, (1993).

An exogenous nucleotide sequence encoding an RNA molecule can, for example, code for an antisense nucleic acid molecule or a ribozyme. An antisense nucleic acid molecule can be complementary to a nucleotide sequence encoding a portion of a protein and thereby selectively hybridize to the gene encoding that protein in a cell. By directly hybridizing to the gene, the antisense nucleic acid molecule can reduce or inhibit transcription of the RNA encoding the protein. Also, by directly hybridizing to the message encoding a protein, the antisense nucleic acid molecule can reduce or inhibit translation, processing and cell stability or half-life of the message, thereby reducing expression of the protein. The exogenous nucleotide sequence can also encode a ribozyme that can specifically cleave RNA encoding a particular cell protein, and therefore reduce or inhibit the expression level of the protein.

The expression of an exogenous nucleotide sequence contained within a recombinant viral vector can be controlled by a number of cis-acting elements contained in the vector. These elements can include a promoter, enhancer, RNA processing signals such as a splice signal and a polyadenylation signal, RNA degradation signal, and translation control signal. In some cases, these signals can be provided as a single unit obtained, for example, as a segment of genomic eukaryotic DNA. However, in many cases, the various elements required to support expression of an exogenous gene in a viral vector will need to come from sources other than the original source of the gene. It should be understood that cis-acting elements that control expression do not function completely independently of each other. There are preferred as well as non-functional combinations of these elements and, therefore, the choice of a particular set of cis-acting elements depends on the degree of expression control desired, the level of expression needed as well as the type of cell used for expression.

The recombinant viral vector requires a promoter to enable a cellular RNA polymerase to bind and transcribe an exogenous nucleotide sequence. Promoters can be viral in origin or can be derived from a cellular gene. The promoter is generally composed of a TATAA box and a CAAT box, often found approximately 30 and 80 base pairs (bp) upstream of the mRNA start site, respectively. Examples of viral-derived promoters that can be used to drive exogenous nucleotide sequence transcription include the SV40 early promoter, the Rous sarcoma virus promoter, the adenovirus major late promoter, the cytomegalovirus early immediate early promoter and the retroviral U3 region promoter of the long terminal repeats (LTRs).

Additional control over expression of an exogenous nucleotide sequence in a viral vector can be provided by including one or more enhancer elements in the viral vector. Enhancers generally encompass a variety of core sequences that act to increase transcription of a promoter from ten to one hundred fold. Strong enhancers of viral origin that are active in a variety of cells include, for example, enhancers derived from SV40, Rous sarcoma virus LTR and the human cytomegalovirus.

A tissue specific enhancer can be used to restrict the expression of an exogenous nucleotide sequence to a particular type of cells. As used herein, the term "tissue specific enhancer" refers to an enhancer that can be activated in a specific cell type resident in a specific tissue. Tissue specific enhancers have been derived from many cellular genes which exhibit tissue specific expression. For example, immunoglobulin enhancers can be used to restrict expression to B lymphocytes, while the muscle creatine kinase enhancer can restrict expression to muscle cells. To achieve tissue specific expression of an exogenous nucleotide sequence in a viral vector, an expression cassette containing this sequence under control of a tissue specific promoter and enhancer should be located within the vector at a site not transcribed by other promoters in the vector. For example in the case of a retrovirus, an expression cassette containing the exogenous nucleotide sequence can be inserted in reverse orientation to avoid transcription by a promoter resident in the LTRs (Dzierzak and Mulligan *Adv. Exp. Med. Biol.* 241:41–43 (1988).

If an exogenous nucleotide sequence is cytotoxic, an inducible expression system that is regulated by an external stimulus can be used. Particular promoters and associated enhancer elements that can regulate transcription in an inducible manner are known to those in the art (see, for example, Kreiger, supra, 1990). Examples of inducible promoters and enhancers that can be used to control exogenous nucleotide sequence expression include metallothionein promoter that is responsive to certain heavy metals and the glucocorticoid promoter from the mouse mammary tumor virus LTR region.

In selecting an inducible vector system for expressing a particular exogenous nucleotide sequence, it is important to ensure that the inducing stimulus does not interfere with the activity of the induced protein or RNA. It is also important to know what level of expression is required for the product encoded by the exogenous nucleotide sequence, since many inducible systems that yield high levels of induction often exhibit lower overall levels of expression than do constitutive control systems. One skilled in the art can use the methods disclosed in the present invention to select an appropriate inducible or constitutive promoter and enhancer necessary to achieve the desired expression level and control of expression for the exogenous nucleotide sequence under consideration.

Exogenous nucleotide sequences in the viral vector that encode a protein can, in most cases, be used as a cDNA sequence without the inclusion of introns for expression in mammalian cells. The choice of a cDNA helps to meet the size limitations of the nucleic acid molecule of many viral vectors as well as simplifies cloning. However, if the expression level is not sufficient, an intron can be included with the exogenous nucleotide sequence. The intron may be derived, for example, from a viral gene such as from SV40 small T antigen or from a cellular gene such as the immunoglobulin gene or from the same natural gene that gave rise to the exogenous nucleotide sequence.

The expression level of genes in mammalian cells can be affected by the presence of a polyadenylation site located at the 3' end of the mRNA. A typical polyadenylation site includes a highly conserved AAUAAA sequence located 11–30 bp upstream of the polyadenylation site and a less well conserved uridine rich or guanine+uridine rich nucleotide tract located downstream of the polyadenylation site. The addition of a polyadenylate tail to the 3' end of mRNA can increase expression level by a factor of 10. Efficient signals for polyadenylation of an exogenous nucleotide sequence can be derived, for example, from the SV40 early transcription unit, the hepatitis B surface antigen transcription unit, and the mouse β-globin gene.

The level of expression of an exogenous nucleotide sequence encoding a protein can be effected at the level of translation. For example, a particular sequence surrounding the initiator AUG codon and the absence of RNA secondary structure surrounding the initiator codon can have a significant impact on the level of expression of the associated exogenous nucleotide sequence (see *Methods in Enzymology*, chapter 39 supra, 1990). Trans-acting elements can be used with the present invention to increase the translation efficiency of a mRNA derived from an exogenous nucleotide sequence. Such elements are known in the art and include, for example, elements derived from the adenovirus VA genes.

A recombinant viral vector that contains an exogenous nucleotide sequence can also include a gene coding for a dominant selectable marker. For example, if an expression cassette encoding the dominant selectable marker gene, neomycin phosphotransferase, is included in the viral vector, addition of the antibiotic G418 to the growth medium of a population of cells previously treated with a virus containing this vector can result in the selective growth of cells that contain the viral vector. Dominant selectable markers for expression in eukaryotic cells are known in the art and include, for example, the herpes virus thymidine kinase gene, a mutant form of the dihydrofolate reductase gene, the hygromycin B phosphotransferase gene and the histidinol dehydrogenase gene.

The inclusion of a dominant selectable marker in a recombinant viral vector can also be used to increase the level of expression of an exogenous nucleotide sequence. For example, the glutamine synthetase gene can be amplified in cells exposed to reduced concentrations of glutamine. Introduction and expression of a viral vector containing the glutamine synthetase gene into a cell and subsequent growth of the cell in low concentrations of glutamine can result in increased copies of the viral vector and thus, increased expression in the cell of an exogenous nucleotide sequence contained within the vector.

A dominant selectable marker can also be used to increase expression of an exogenous nucleotide sequence in a mammalian cell by way of a polycistronic expression vector. In such a vector, the first cistron can be occupied by the exogenous nucleotide sequence while the second cistron can be occupied by a dominant selectable gene. Since the translation of the selectable gene located in the second cistron is less efficient that of the first cistron, the addition of a selective drug to the culture medium can select a population of cells that express higher levels of viral mRNA, and consequently express higher levels of the first cistron product than would a non-selected population of cells. Polycistronic viral expression vectors are known in the art. A polycistronic viral expression vector can also be used to express more than one exogenous nucleotide sequence.

A recombinant viral vector of the present invention can include certain features to make it safe for human use. For example, the vector can include a "suicide gene", which can be activated by providing an external stimulus, resulting in the death a cell which harbors the suicide gene. A suicide gene that can be used with the present invention include, for example, the herpes virus thymidine kinase gene that is activated by gangcyclovir (Culver et al. *Science* 256: 1550–1552 (1992). Another safety feature is to disable the virus once it gets inserted into the chromosome of the target cell. Such retroviral vectors are known as "suicide vectors" or "self inactivating vectors" and they contain deletions in the promoter/enhancer regions of the 3'LTR. During transcription by reverse transcriptase, mutations in the 3' LTR become incorporated into both LTRs of the integrated retrovirus. Such mutations reduce the likelihood of producing a full length viral mRNA for packaging into virions and reduce the likelihood of activating cellular genes nearby the LTRs.

A recombinant viral vector of the present invention can also be non-replicating. Such a vector can be used to generate infectious virus containing an exogenous nucleotide sequence that is unable to replicate after infecting a target cell. For example, various types of non-replicating retroviral vectors are known in the art that are lacking the GAG, POL an ENV genes required to package an infectious retroviral virion. For such a vector, infectious virus is produced by inserting the vector into a "packaging cell line". Examples of packaging cells lines such as PA317 and ψCRIP are known in the art are their use for the present invention is detailed in Example I.

The invention also provides processes to produce a stabilized virus. The processes involve contacting a virus producing cell at a temperature less than 37° C., particularly less than about 30° C., with a culture medium containing a stabilizing agent, under conditions suitable to produce the stabilized virus. The stabilized virus of the invention can be purified by methods well known to those in the art. Such methods include, for example, cross-flow filtration (Kotani et el, supra, (1994), which is incorporated herein by reference) or ultracentrifugation (Rettinger et al. *Proc. Natl. Acad. Sci.* (USA), 91:1460–1464 (1994), which is incorporated herein by reference).

As used herein, the term, "virus producing cell" means a cell that when placed in culture can produce infectious virus in the culture medium. The process of culturing a virus producing cell to obtain culture medium containing infectious virus or viral broth is defined herein, as a production culture. For example, culture of a packaging cell line producing a recombinant retrovirus is considered a production culture if the medium containing the virus is taken and used as a source of infectious virus (see Example I). As used herein, the term "viral broth" means the cell culture medium from a virus producing cell that contains infectious virus. As used herein, the term "infectious virus" is a virus that is capable of transferring it's nucleic acid vector into a cell resulting in expression in the cell of an exogenous nucleotide sequence contained within the vector.

The optimal temperature for producing a stabilized virus using a particular stabilizing agent can be determined using the methods described in Example I. For example, Lipid Concentrate (Gibco/BRL) is a stabilizing agent that enhances 37° C. infectivity half-life of retrovirus produced in cultures maintained at 29° C. but not at 37° C. or 33° C. (see Tables I through III). For some viral producing cells, such as the pMFG/ψCRIP, the production of virus at 29° C. in the absence of any stabilizing agents can, by itself, result in a higher infectivity half-life at 37° C. than virus produced at 37° C. (see Table III). In this case, the addition of a stabilizing agent to pMFG/ψCRIP cells producing retrovirus at 29° C. results in a further increase in viral infectivity half-life than achieved by the production of virus at 29° C. alone (see Tables II and III).

A stabilizing agent can consist of one compound or a combination of compounds. For example, the present invention provides the stabilizing agent Lipid Concentrate which contains a mixture of cholesterol, cod liver oil, Pluronic® F-68, d-α-tocopherol acetate and Tween 80™. A stabilizing agent can consist of a single compound, such as Pluronic® F-68, which is a component of Lipid Concentrate that is capable of performing as a viral stabilizing agent (see Tables II and III). The optimal concentration of a stabilizing agent such as Pluronic® F-68 for producing a stabilized virus can be determined by performing a dose response experiment as exemplified in Table IV.

Where a combination of compounds is desirable, the optimal concentration of each compound in the stabilizing agent can be determined using the methods described in Example I. It is recognized, for example, that the effective concentration of a component of the stabilizing agent can vary with the temperature of viral production, pH of the culture medium, type of culture medium used, the presence of other components of the stabilizing agent and the target cells to be infected. However, in view of the methods disclosed in Example I, one skilled in the art can readily determine the appropriate concentration of stabilizing agent to achieve desired enhancement of viral infectivity.

The extent of stabilization of the stabilized virus, produced by the methods disclosed herein, can be measured by determining viral infectivity and calculating a viral infectivity half-life. Methods to measure viral infectivity are well known in the art (see Krieger (supra, 1990) and Goeddel (supra, 1990)). Example I provides methods to measure viral infectivity and to calculate a viral infectivity half-life at a particular temperature.

The disclosed process for producing a stabilized virus involves culturing viral producing cells in culture medium containing a stabilizing agent. The invention also provides for the ability to obtain a stabilized virus by adding the stabilizing agent to the virus after the virus has already been produced. Thus, the post-culture addition of Pluronic® F-68 and Tween 80™ to a pMFG/ψCRIP viral broth harvest, produced at 29° C., resulted in a 38% increase in 37° C. infectivity half-life compared to virus produced in regular medium at 37° C. (see Table V). A stabilizing agent also can be added to virus previously processed, such as by concentrating, from a viral broth produced at a temperature less than 37° C.

If desired, the stabilizing effect can be made non-reversible by selecting a particular stabilizing agent. Non-reversibility can occur, for example, if the compounds of the stabilizing agent were integral to the viral envelope and, therefore, maintained their association with the virus after the source of stabilizing agent was removed. Non-reversibility can, for example, be desirable if the virus is used for infection after processing, such as by purification, or by diluting the viral broth into medium lacking the stabilizing agent.

Non-reversibility of a stabilized virus of the present invention can be determined by processing each stabilized viral preparation into two sample groups. The first sample group is obtained by diluting a viral broth into culture medium containing the stabilizing agent at the same concentration as was used in the original production culture. The second sample group is obtained by diluting the same viral broth into culture medium without the stabilizing agent. The two sets of dilutions are incubated at 37° C., then assayed for viral infectivity as described in Example I. If the stabilized effect is non-reversible, the two sample groups will have the same half-life. However, if the stabilizing effect is reversible, the infectivity of the second sample group is reduced relative to the first sample group.

The invention also provides a method for introducing an exogenous nucleotide sequence into a target cell using a stabilized recombinant virus that contains a viral vector incorporating the exogenous nucleotide sequence. As described above, the stabilized recombinant virus useful for the present invention can be an RNA or a DNA virus and can contain viral nucleic acid incorporating an exogenous nucleotide sequence within an expression cassette. Also as described above, the exogenous nucleotide sequence can encode proteins or RNA such as antisense RNA or an RNA ribozyme.

As used herein, the term "target cell" refers to a cell infected by a stabilized virus of the present invention. The present invention provides methods to introduce an exogenous nucleotide sequence into a target cell using a stabilized virus containing a viral vector incorporating the exogenous nucleotide sequence. This method provides contacting a target cell with any of the stabilized viruses described herein under suitable conditions. The contacting can be effected in vitro, ex vivo, or in vivo using methods well known in the art and using an effective amount of stabilized virus. The invention also provides a composition comprising a cell containing an exogenous nucleotide sequence delivered by a stabilized virus whose viral vector incorporates the exogenous nucleotide sequence.

Target cells suitable for the present invention can include, for example, bone marrow cells, lymphocytes, fibroblasts, keratinocytes, hepatocytes, endothelial cells, neurons, muscle cells, and epithelial cells. Such cells can be obtained, for example, from a patient or subject to be treated or from a subject that is sufficiently histocompatible to the subject being treated. Thus, the cells can be autologous or can be heterologous cells such as allogeneic cells obtained from a cell repository. Also, target cells can be derived from any animal or mammal, including but not limited to rat, murine, bovine, porcine, equine, canine, feline, primate or human.

It will be necessary to consider the nature and source of the target cells to be infected when choosing the culture medium and stabilizing agent for preparing the stabilized virus. The optimal culture medium and stabilizing agent are chosen to achieve a stabilized virus and to support infection and growth of the target cells.

The present invention provides a method to administer a stabilized virus to a subject. "Subject" means any animal, mammal, rat, murine, bovine, porcine, equine, canine, feline primate or human patient. Such administration can be useful for treating various diseases through genetic therapy. The various diseases include, for example, those of the liver and lung, cancer, clotting disorder or circulating gene product disorder, viral disease, such as acquired immunodeficiency syndrome, immunization and transplantation, and genetically inherited disease. In addition, administration of a stabilized virus to a subject can be used to elicit an immune response to a protein, carbohydrate, lipid or nucleic acid molecule associated with the virus.

The choice of stabilized virus for particular disease applications can depend on the approach considered for therapy. For example, a recombinant adenovirus can be used to infect epithelial cells such as cells of the lung or liver. As herpes virus has a natural ability to infect neural cells, a stabilized recombinant herpes virus produced by the disclosed method can be used to treat neural diseases.

The type of exogenous nucleotide sequence chosen for inclusion into a recombinant vector of a stabilized virus to be administered to a subject depends of the type of disease being treated. For example, a subject afflicted with cystic fibrosis can be administered a stabilized virus that contains an exogenous nucleotide sequence encoding the cystic fibrosis transmembrane conductance regulator. The type of nucleotide sequence chosen for a particular disease can also depend on the approach used for treatment. Thus, in the case of acquired immunodeficiency syndrome, the subject can be administered a stabilized virus containing an exogenous nucleotide sequence encoding a soluble CD4 protein or encoding an anti-sense RNA or a RNA ribozyme specific for a viral RNA.

Any of the viral expression vectors described herein are useful to produce a stabilized virus for diagnosis or therapy of disease. When used pharmaceutically, the stabilized virus can be combined with various pharmaceutically acceptable carriers, such as saline and the like. Suitable pharmaceutically acceptable carriers are well known to those of skill in the art. As used herein, the term "pharmaceutically acceptable carrier" encompasses any of the standard pharmaceutical carriers, such as a phosphate buffered saline solution, water, and emulsions, such as oil/water or water/oil emulsion, and various wetting agents. The compositions also can include stabilizers and preservatives. For examples of carriers, stabilizers and adjuvants, see Martin, *Remington's Pharm. Sci.*, 15th Ed. (Mack Publ. Co., Easton, 1975), incorporated herein by reference.

The composition of a stabilized virus and a pharmaceutically acceptable carrier can be administered therapeutically or prophylactically in vivo or ex vivo. As used herein, "administering" includes but is not limited to introducing into a cell or subject intravenously, by direct injection or instillation, by intraperitoneal administration, by aerosol administration to the lungs, or by oral administration. Administration can be effected continuously or intermittently and the effective amount will vary with the subjects weight, health and so forth. Administration also can performed ex vivo by, for example, introducing the stabilized virus into a shunt through which cells of the subject flow from one part of the body to another.

As used herein, the term "effective amount" means the effective dosage of the composition to treat a particular condition and will vary with the pathology, disease, patient status, and other factors well known to those of skill in the art. An effective amount is easily determined by those of skill in the art.

The present invention also provides an in vitro utility for a stabilized virus containing an exogenous nucleotide sequence encoding a protein or polypeptide. Target cells infected with such a stabilized virus can be used to produce the protein encoded by the nucleotide sequence. As used herein, "protein" means the full sized protein encoded by a full length gene as well as any portions of the protein. Any polypeptide composition that can be produced by a cell is included in the meaning of protein.

Cells infected with the stabilized virus can be grown under conditions that favor transcription and translation of the exogenous nucleotide sequence resulting in production of the protein by the cells. The stabilized virus is more suitable for this procedure than a non-stabilized virus, since the stabilized virus, by virtue of a longer infectivity half-life at 37° C., can infect a greater fraction of cells in a cell population, therefore resulting in more protein production than can be achieved with a non-stabilized virus.

The protein produced by an infected cell can associated with the cell or can be secreted into the culture medium. Secretion into the culture medium is accomplished by inserting a nucleotide sequence encoding a secretory signal sequence at the 5' end of the exogenous nucleotide sequence to be produced. Secretory signal sequences are well known in the art. The protein encoded by the exogenous nucleotide sequence can then be isolated or purified from the cells or the culture medium using well known methods in the art. As used herein, "isolated" or purified means substantially free of native proteins or nucleic acids normally associated with the protein in the cell.

The use of a stabilized virus of this invention to prepare medicaments for the treatment of a disease or for therapy is further provided by this invention.

EXAMPLE I

Production of Stabilized Virus

This example describes processes and methods to produce and evaluate a stabilized virus.

A. Cell Lines

Amphotrophic pMFG retroviruses that contain a functioning LacZ gene were produced by the ψCRIP packaging cell line (Danos and Mulligan, *Proc. Natl. Acad. Sci (USA)* 85:6460–6464 (1988) which is incorporated herein by reference) and by the PA317 packaging cell line (Miller and Buttimore, *Molec. Cell. Biol.* 6:2895–2902 (1986), which is incorporated herein by reference). PA317 cells are available from the American Type Culture Collection (CRL 9078, Rockville, Md.). In addition to the LacZ gene, the pMFG retroviral vector includes retroviral LTRs and a ψ packaging signal. The pMFG/ψCRIP and pMFG/PA317 retrovirus producing cells can be made by incorporating the pMFG retroviral vector into the ψCRIP and PA317 packaging cell lines by a transfection method (for example see Ausubel et al., in *Short Protocols in Molec. Biol.*, 2nd edition, (Greene Publishing Assoc. and Wiley and Sons, New York, N.Y., pages 9–36 to 9–41, 1992), which is incorporated herein by reference). Methods to produce retroviral vectors and generate incompetent retroviruses are know in the art (for example, see Stoker (supra, 1993)).

Viral packaging cells were cultured in Dulbecco's Modified Eagle's Medium (DMEM, Sigma Chemical Co. St. Louis, Mo.) containing 10% calf serum (standard medium). Packaging cell cultures were incubated at either 29° C., 33° C. or 37° C. in an atmosphere containing 5% $CO_2$. The target cell line used for infectivity testing was the CV-1 fibroblast cell line (CCL-70, American Type Culture Collection) derived from the African green monkey. For infectivity assays, confluent cultures of CV-1 target cells, previously cultured in standard medium, were harvested by treatment with trypsin-EDTA (Gibco/BRL, cat#15400-039) and were seeded into six well plates (Costar Corp, Cambridge, Mass.) at about 30,000 cells/well and were cultured for 24 hours prior to virus exposure.

B. Production of a Viral Broth by Virus Producing Cells

The packaging cell lines producing the amphotrophic pMFG retroviruses were cultured in standard culture medium with or without the stabilizing agent. Stabilizing agents tested include Lipid Concentrate used at 2× the manufacturer's recommended dose (Gibco/BRL, Gaithersburg, Md., catalog no. 21900-014), Pluronic® F-68 (0.6 g/L or 2.0 g/L, Gibco/BRL, catalog no. 24040-016) and Tween 80™ (0.05 g/L, Sigma, catalog no. P-1754). Medium containing Lipid Concentrate used at a 2× concentration contains cholesterol (9 mg/ml), cod liver oil (20 mg/ml), Pluronic® F-68 (2 g/L), d-α-tocopherol acetate (4 mg/ml) and Tween 80™ (0.05 g/L). Cultures containing a stabilizing agent were incubated in 10 cm tissue culture dishes or in 75 $cm^2$ tissue culture flasks (Falcon Labware, Franklin Lakes, N.J. or Gibco/BRL) at various temperatures for a period of at least 36 hr in duration and ending just prior to culture confluence. Only one type of culture vessel was used within each experiment. Following incubation, viral broth was removed from the cells and passed through 0.45 μm filters (Gelman Sciences, Ann Arbor, Mich.) that had been preconditioned with standard culture medium to minimize binding of virus to the filter. The filtered viral broth was then aliquoted, frozen and stored at −80° C. For the freezing procedure, up to 4 ml of viral broth was placed in a cryotube and frozen by exposing to −80° C. air. Thawing of samples is accomplished by immersing the cryotubes in 37° C. water.

C. Determination of Viral Infectivity Half-Life

Viral broth was thawed and incubated for various amounts of time at 37° C. prior to evaluating viral infectivity. Typical incubation times were 24, 16, 8 and 0 hours. After incubation at 37° C., infection medium was formulated as follows: for each well of a six well plate, one ml of medium conditioned by the CV-1 cells (conditioned by exposure of 2 ml of medium per 30,000 CV-1 cell for 24 hr) was mixed with a 1 ml or less of viral broth (sufficient to produce an infectious titer of about 20 to 300 colony forming units (CFUs) per 30,000 CV-1 cells) together with additional fresh medium to make the final volume up to 2 ml. A suitable level of viral broth dilution was estimated from previous experiences with the producing cell line. Additionally, the infectious medium contained polybrene at 4.4 μg/ml (Aldrich Chemical Co., Milwaukee, Wis.). To determine viral infectivity, the formulated infection media were added (2 ml/well in triplicate) to cultures of seeded CV-1 target cells. The cells were cultured for 6–8 hours (period fixed within each experiment), the medium was removed and replaced with 2 ml of fresh culture medium and the cells were cultured for several days to achieve 3–5 post-infection cell divisions prior to staining with X-gal.

Viral infectivity was determined by staining infected cells with X-gal substrate and counting CFUs. Culture wells containing infected cells were washed 2× with 1.5 ml of Hank's Balanced Salt Solution (HBSS, Gibco/BRL) and fixed with 1.5 ml of 2.1% (v/v) formaldehyde (Sigma) and 0.2% (v/v) glutaraldehyde (Sigma) for 5 min at room temperature. Following fixation, the cells were washed 2× with 1.5 ml of HBSS, then 1.5 ml staining solution was added (Staining solution contains 50 μL of 20 mg/ml X-Gal powder (5-bromo-4-chloro-3 indolyl-β-D-galactoside) dissolved in N,N-dimethylformamide (Sigma) added fresh to each 0.95 ml of phosphate buffered saline containing 5 mM $K_3Fe(CN)_6$ (Sigma), 5 mM $K_4Fe(CN)_6 \cdot H_2O$ (Sigma) and 2 mM $MgCl_2$ (Sigma). The cells were incubated with staining solution for 3 days at 37° C. to allow the blue color to develop in the infected cells. A CFU was defined as a cluster of blue-stained cells which were visualized using an inverted light microscope.

The infectivity half-life of virus was determined by the following procedure: 1) The number of CFUs for each condition was determined at each dilution and multiplied by the dilution factor to obtain the total number of CFUs (or viral titer) in undiluted viral broth for each time point; 2) The mean viral titer value for each time point was determined by averaging the calculated viral titers obtained from each dilution tested; 3) The fraction of remaining viral titer was determined for each time point relative to the titer of the zero time incubation time point; 4) A graph was produced by plotting the natural log of the fraction of remaining viral titer for each time point on the Y axis versus time on the X axis; and 5) a line was drawn through the points on the plot by linear regression and the slope of the line when divided into the natural log of 0.5 was taken as the viral infectivity half-life (equal to −0.6931÷slope).

D. Evaluation of Production Temperature and Stabilizing Agent on Viral Stability The stability of virus produced at various temperatures in media supplemented with or without a stabilizing agent was determined by measuring the viral infectivity half-life at 37° C. (see Table I). In these experiments, addition of 2× Lipid Concentrate to production cultures of the pMFG/PA317 retrovirus producing cell line and growth of the production culture at 37° C. or at 33° C. showed little if any affect on the 37° C. viral infectivity half-life. In contrast, addition of 2× Lipid Concentrate to a production culture of pMFG/PA317 cells grown at 29° C. showed about 100% increase in the 37° C. infectious half-life of resulting viral broth. A Similar increase (about 50%) in 37° C. viral infectivity half-life was observed when retroviruses were produced by pMFG/ψCRIP cells cultured at 29° C. in medium containing 2× Lipid Concentrate (Table I).

TABLE I

PRODUCTION OF A STABILIZED RETROVIRUS BY CULTURE AT REDUCED TEMPERATURE WITH A STABILIZING AGENT

| Viral Producing Cell | 37° C. Infectivity Half-Life (hr) | | | | | |
|---|---|---|---|---|---|---|
| | Standard Medium | | | Standard Medium + Lipid Concentrate (2x) | | |
| | 37° C. | 33° C. | 29° C. | 37° C. | 33° C. | 29° C. |
| pMFG/ PA317 | 9.2 | 8.0 | 9.9 | 8.5 | 10.7 | 18.1 |
| pMFG/ ψCRIP | 9.1 | nd* | 9.0 | 10.7 | nd | 14.0 |

*not done

Two components of Lipid Concentrate, Pluronic® F-68 and Tween 80™ were then tested for their ability to produce stabilized virus. The 37° C. infectivity half-life was determined for retrovirus from pMFG/PA317 (Table II) and pMFG/ψCRIP (Table III) cells cultured at 29° C. or 37° C. in standard culture medium or in culture medium containing a stabilizing agent. Ratios of the 37° C. half-lives obtained for the various conditions were calculated in order to identify the impact of temperature and the addition of a stabilizing agent, either separately or combined, on viral stability. The results in tables II and III represent several experiments where Pluronic® F-68 was tested by itself or together with Tween 80™ or as a component of Lipid Concentrate. The average of all experiments for each cell line show that 37° C. viral infectivity half-life is most enhanced when Pluronic® F-68 was added to a 29° C. production culture.

TABLE II

PRODUCTION OF STABILIZED pMFG/PA317 RETROVIRUS USING VARIOUS STABILIZING AGENTS AND PRODUCTION TEMPERATURES

| Stabilizing Agent | | | 37° C. Infectivity Half-Life Ratio* | | | |
|---|---|---|---|---|---|---|
| Lipid Conc. ** | Pluronic® F-68 | Tween 80 ™ | 29R/ 37R | 37X/37R | 29X/29R | 29X/37R |
| + | − | − | 1.07 | 0.92 | 1.83 | 1.96 |
| + | − | − | 0.58 | 0.69 | 1.93 | 1.12 |
| − | + | − | 1.36 | 0.92 | 1.26 | 1.72 |
| Average | | | 1.00 | 0.91 | 1.63 | 1.53 |
| Standard Deviation | | | 0.39 | 0.21 | 0.44 | 0.42 |

TABLE II-continued

*"29" and "37" refer to the temperature of viral production (°C.) while "R" means regular culture medium and "X" means culture medium plus a stabilizing agent.
**Lipid Concentrate

TABLE III

PRODUCTION OF STABILIZED pMFG/ΨCRIP RETROVIRUS USING VARIOUS STABILIZING AGENTS AND PRODUCTION TEMPERATURES

| Stabilizing Agent | | | 37° C. Infectivity Half-Life Ratio* | | | |
|---|---|---|---|---|---|---|
| Lipid Conc.** | Pluronic® F-68 | Tween 80™ | 29R/37R | 37X/37R | 29X/29R | 29X/37R |
| + | – | – | 0.98 | 1.17 | 1.56 | 1.53 |
| – | + | + | nd*** | nd | 1.44 | nd |
| – | + | – | nd | nd | 1.16 | nd |
| – | + | + | nd | nd | 1.26 | nd |
| – | + | + | nd | nd | 1.81 | nd |
| – | + | – | 1.26 | 0.93 | 1.19 | 1.50 |
| – | + | – | 1.47@ | 0.99@ | 0.77@ | 1.13@ |
| Average | | | 1.24 | 1.03 | 1.31 | 1.39 |
| Standard Deviation | | | 0.25 | 0.12 | 0.33 | 0.22 |

"29" and "37" refer to the temperature of viral production (°C.) while "R" means regular culture medium and "X" means culture medium plus a stabilizing agent.
**Lipid Concentrate.
***"nd" means not done.
@Half-life determined in the presence of polybrene at 4.3 μg/ml.

The concentration (conc.) of Pluronic® F-68 necessary to produce an increase in viral stability was assessed in pMFG/ψCRIP retrovirus producing cultures (Table IV). Although the pMFG/ψCRIP retrovirus shows a 36% increase in 37° C. infectivity half-life by reducing the production culture to 29° C. alone (see 29R/37R in Table IV) the addition of 0.6 g/L Pluronic® F-68 to the 29° production culture showed an increase in viral stability as compared to 29° C. production temperature alone (41% increase versus 36% increase). The addition of increasing amounts of Pluronic® F-68 to the 29° production culture continued to show increases in viral 37° C. infectivity half-life (52% increase at 2 g/L and 72% increase at 6 g/L) which were clearly greater than that obtained by a 29° C. production temperature alone.

TABLE IV

DOSE RESPONSE OF A STABILIZING AGENT ON THE STABILITY OF RETROVIRUS PRODUCED BY pMFG/ΨCRIP CELLS

| Stabilizing Agent | 37° C. Infectivity Half-Life Ratio* | | | |
|---|---|---|---|---|
| Pluronic® F68 (g/L) | 29R/37R | 37X/37R | 29X/29R | 29X/37R |
| 0.6 | 1.36 | 0.86 | 1.04 | 1.41 |
| 2.0 | 1.36 | 1.11 | 1.12 | 1.52 |
| 6.0 | 1.36 | 0.92 | 1.26 | 1.72 |

*"29" and "37" refer to the temperature of viral production (°C.) while "R" means regular culture medium and "X" means culture medium plus a stabilizing agent.

The invention also provides for the ability to obtain increased viral stability by adding the stabilizing agent to the virus after completion of the viral production culture. The addition of Pluronic® F-68 and Tween 80™ to a pMFG/ψCRIP production culture grown at 29° C. showed a 38% increase in 37° C. infectivity half-life compared to virus produced in regular medium at 37° C. (table V).

TABLE V

EFFECT OF POST CULTURE ADDITION OF THE STABILIZING AGENT PLURONIC® F68 (2 g/L) and Tween 80 (0.05 g/L) ON THE STABILITY OF pMFG/ΨCRIP RETROVIRUS

| 29R/37R | 37X/37R | 29X/29R | 29X/37R |
|---|---|---|---|
| 1.17 | 0.94 | 1.18 | 1.38 |

*"29" and "37" refer to the temperature of viral production (°C.) while "R" means regular culture medium and "X" means culture medium plus a stabilizing agent.

Although the invention has been described with reference to the example described above, it should be understood that various modifications can be made without departing from the spirit of the invention. Accordingly, the invention is limited only by the claims.

We claim:

1. A stabilized retrovirus composition comprising a retrovirus and an α-hydro-ω-hydroxypoly(oxyethylene)poly-(oxypropylene)poly(oxyethylene) block copolymer.

2. The stabilized retrovirus composition of claim 1, wherein the α-hydro-ω-hydroxypoly(oxyethylene)poly(oxypropylene)poly(oxyethylene) block copolymer is PLURONIC® F-68.

3. A method for introducing an exogenous nucleotide sequence into a target cell in vitro or ex vivo, comprising contacting the target cell with the stabilized retrovirus composition of claim 1.

4. The stabilized retrovirus composition of claim 1 or 2 further comprising cholesterol, cod liver oil, d-α-tocopherol acetate and TWEEN 80™.

5. The stabilized retrovirus composition of claim 1 or 2, further comprising a target cell.

6. A process for producing a stabilized retrovirus comprising the steps of:

a) obtaining a retrovirus producing cell;

b) contacting the retrovirus producing cell with a culture medium comprising an α-hydro-ω-hydroxypoly(oxyethylene)poly(oxypropylene)poly (oxyethylene) block copolymer at a temperature less than 37° C.; and c) producing retrovirus from the retrovirus producing cell.

7. The process of claim 6, wherein the α-hydro-ω-hydroxypoly(oxyethylene)poly(oxypropylene)poly(oxyethylene) block copolymer is PLURONIC® F-68.

8. The process of claim 6 or 7, wherein the culture medium further comprises cholesterol, cod liver oil, d-α-tocopherol acetate and TWEEN 80™.

9. The process of claim 6 or 7, wherein the temperature is less than about 30° C.

10. The process of claim 6 or 7, comprising the additional step of purifying the retrovirus.

11. A stabilized virus produced by the process of claim 6 or 7.

12. The process of claim 8 wherein the temperature is less than about 30 C.

13. The process of claim 8, comprising the additional step of purifying the retrovirus.

14. A stabilized retrovirus produced by the process of claim 8.

15. The process of claim 9, wherein the temperature is about 29° C.

* * * * *